United States Patent [19]

Sirica

[11] Patent Number: 4,967,587
[45] Date of Patent: Nov. 6, 1990

[54] IMPACT CALIBRATION TOOL
[75] Inventor: Edward G. Sirica, Hartford, Conn.
[73] Assignee: Combustion Engineering, Inc., Windsor, Conn.
[21] Appl. No.: 424,484
[22] Filed: Oct. 20, 1989
[51] Int. Cl.$^5$ ............................................. G01C 17/38
[52] U.S. Cl. ..................................... 73/1 D; 376/245; 173/120; 173/121; 73/12
[58] Field of Search ................ 376/245; 173/120, 121; 73/12, 1 D

[56] References Cited

U.S. PATENT DOCUMENTS

| | | | |
|---|---|---|---|
| 4,346,768 | 9/1982 | Ross | 173/118 |
| 4,622,202 | 11/1986 | Yamada et al. | 376/246 |
| 4,682,490 | 7/1987 | Adelman et al. | 73/12 |

Primary Examiner—Stephen J. Lechert, Jr.
Assistant Examiner—N. Bhat
Attorney, Agent, or Firm—John H. Mulholland

[57] ABSTRACT

A tool 10 for creating a standard repeatable impact on a nuclear steam supply system (NSSS) structure to determine the response of an accelerometer to the impact of a known energy at a predetermined location on the structure. The tool 10 includes a barrel 12 and a spring 30 which biases a ram 20 reciprocally mounted in the barrel and driven by cam plates 66 and 68 on shaft 60. A flange 28 on ram 20 compresses spring 30 and upon movement of follower 72 to a maximum radial distance from shaft 60, the follower 72 drops down step 70 on the cam surface to allow spring 30 to uncompress and project ram 20 out of the barrel such that end 22 of the ram creates a standard impact on the NSSS structure. A hand crank drives shaft 60. A dampening spring 78 assists in the rebound of the ram 20.

6 Claims, 2 Drawing Sheets

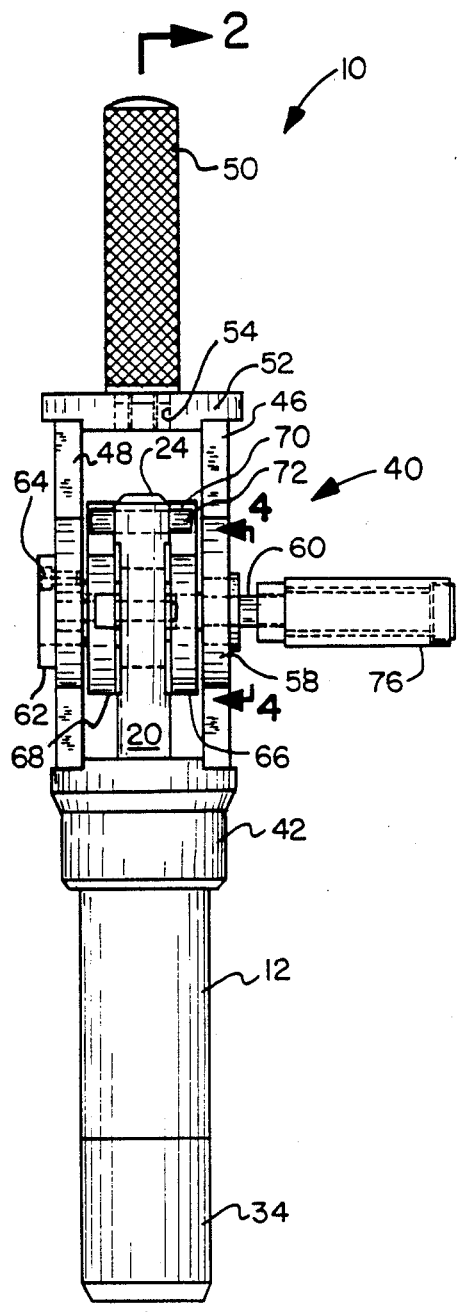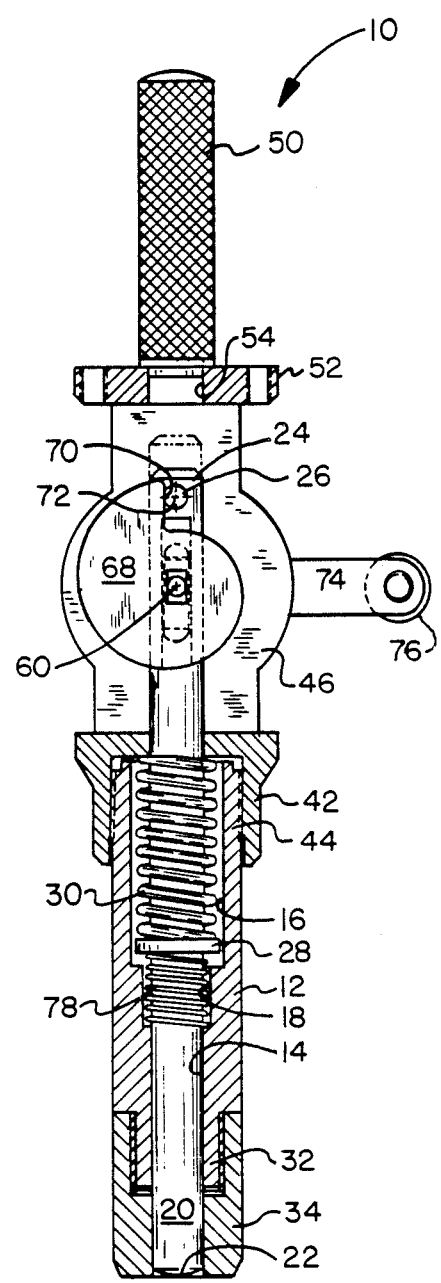
Fig. 1
Fig. 2

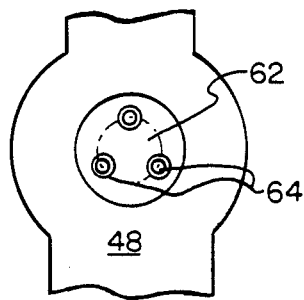
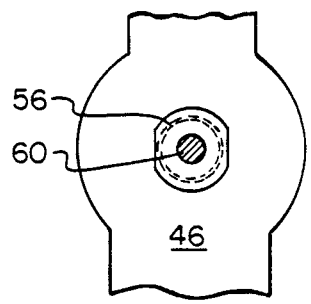
Fig. 3　　　　Fig. 4
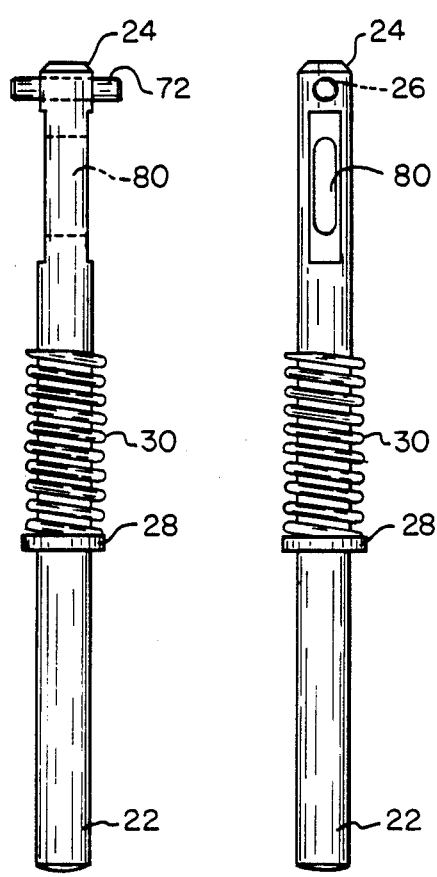
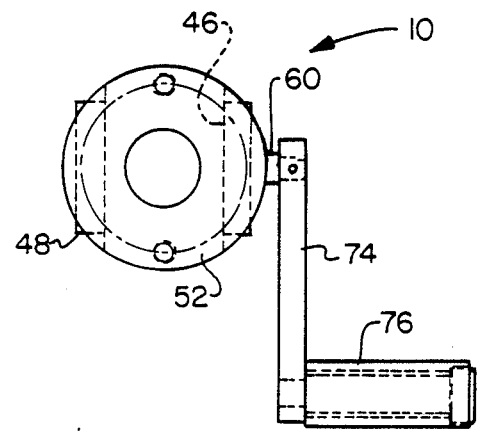
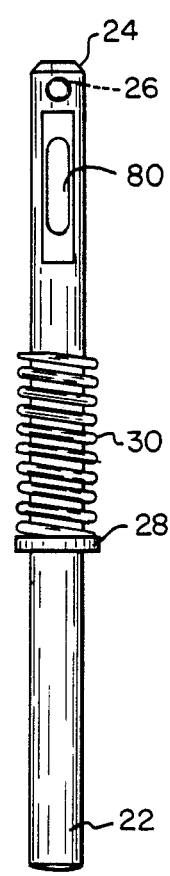
Fig. 5
Fig. 6　　Fig. 7

IMPACT CALIBRATION TOOL

BACKGROUND OF THE INVENTION

The invention relates to an impact calibration tool for use in a loose parts monitoring system of the type used in an operative nuclear steam supply system (NSSS) to avoid the potential of a long shutdown to repair reactor internals. There is a danger, especially immediately following an outage, that debris in the form of pieces of repair material or tools may remain in the reactor and move with the circulating fluids. Also, it has been known that unsecured fasteners and other parts can vibrate due to this flow. Depending on the mass and velocity of these items, which for convenience are labelled "loose parts", they typically create a vibration frequency of fairly normal distribution in the range of 0.1 to 100 $KH_z$ with the majority of loose parts producing frequencies in the range of 1.0 to 10 $KH_z$.

Loose parts monitoring systems typically are used for detecting, locating and characterizing metallic loose parts in both reactors and steam generators. For a better understanding of these systems, see papers such as: Thompson, J. P., et al, "STOCHASTIC TREATMENT OF LOOSE PART IMPACT SIGNALS", American Nuclear Society, 1983 Winter Meeting; Lubin, B. T., et al, "STATISTICAL ANALYSIS OF LOOSE PART MONITORING SYSTEM SIGNALS TO DIAGNOSE THE PRESENCE OF A LOOSE PART ON THE SECONDARY SIDE OF A PWR STEAM GENERATOR", jt. ASME/IEEE Power Generation Conference, October 1986; and the bibliography papers listed therein.

In order to determine whether loose parts are stationary or roving parts, changes in signals which can indicate change in condition of the suspected loose part are recorded.

The typical equipment set up for monitoring an NSSS utilizes a series of accelerometers (transducers) mounted to record impulse-type signals that could be caused by the impact of a loose part. These signals previously have been calibrated in terms of the response at the accelerometer location to the impact energy of a gravity driven weight impacting the structure at a known location relative to the accelerometer, expressed in "g's" of acceleration. USNRC, Regulatory Guide 1.133 (Ref. 1) establishes minimum functional requirements for a loose parts monitoring system.

SUMMARY OF THE INVENTION

The present invention is a tool for conveniently creating a standard repeatable impact on a NSSS structure to determine the response of an accelerometer to an impact of a known energy at a predetermined location on the structure. The tool increases the accuracy and repeatability of the impact energy over the previous method which used a gravity driven weight impacting on the structure. Its use increases the accuracy of calibration of the series of accelerometers in a loose parts monitoring system.

The tool of the invention has a hollow barrel with an outer end and an inner end. A ram having a first end and a second end is reciprocally mounted within the barrel with the first end for alternate impact producing projection from and retraction into the outer end of the barrel.

A large spring within the barrel engages a flange on the ram to bias the ram in a direction toward the outer end of the barrel and when released to uncompress, the spring drives the ram to project and impact on an adjacent structure against which the barrel end has been placed. This creates the repeatable impact.

A housing is mounted on the inner end of the barrel for bearinged support of a rotatable shaft transversely thereto. The shaft rotationally drives two spaced cam plates which have cam surfaces to drive a follower pin fixed transversely to the adjacent second end of the ram. The cam shape reciprocates the ram and retracts its flange against the large spring to compress the spring. As rotation continues, the cam surface is shaped to release the pin follower so that the spring uncompresses, thus driving the ram to impact. A smaller spring dampens the shock within the tool to prevent damage to the pin, cam surface and flange. A hand crank drives the shaft. One full crank rotation creates one repeatable impact for calibration of the accelerometers. The tool is held by means of a handle on the housing.

BRIEF DESCRIPTION OF THE DRAWINGS

FIG. 1 is a front elevational view of an impact calibration tool constructed according to the principles of the invention;

FIG. 2 is a cross-sectional view of the tool taken along line 2—2 of FIG. 1, with certain of the parts shown in full for clarity;

FIG. 3 is a fragmentary side elevational view of the left side of the tool of FIG. 1;

FIG. 4 is a fragmentary cross-sectional view taken along line 4—4 of FIG. 1;

FIG. 5 is a plan view of the tool of FIG. 1;

FIG. 6 is a front elevational view of the ram, large spring and follower pin of the tool of FIG. 1;

FIG. 7 is a side elevational view of the ram, large opening and pin of FIG. 6.

DETAILED DESCRIPTION OF THE PREFERRED EMBODIMENT

The numeral 10 generally designates the impact calibration tool of the invention for producing a standard repeatable impact on a structure to determine the response of an accelerometer to the impact of a known energy at a predetermined location on the structure.

The tool 10 includes a hollow barrel member 12, having a central bore 14. The barrel 12 is conveniently made of a metal, such as aluminum, and has a larger diameter counterbored portion 16 adjacent a smaller diameter counterbored portion 18.

A ram 20 having a first end 22 for impacting and a second end 24 with a transverse opening 26 is reciprocally mounted within bore 14 of barrel 12. The ram 20 has a flange 28 within the larger counterbore 16.

A large spring 30 acts against the flange 28 in counterbore 14 to bias the ram 20 in a direction toward the outer barrel end 32 adjacent the impacting end 22 of ram 20. A hollow carbon steel end cap 34 is threadedly secured on the outer barrel end 32 to prevent wear thereof.

A hollow cam support housing, generally designated by the numeral 40, has as its base a hollow end cap 42 threadedly secured to the outside of the inner end 44 of the barrel 12. The ram 20 extends through end cap 42 and into the housing 40 with its second end 24 between right and left side plates 46 and 48, respectively, of housing 40. A handle 50 is attached to the top plate 52 of the housing 40 by means of welding.

As seen in FIGS. 3 and 4, the right hand side plate 46 has a threaded opening 56 into which a hollow bearing and lock cap 58 is assembled to rotationally mount and hold a first end of shaft 60. The opposite end of the shaft 60 rotates in a suitable bearing in an aperture in left hand plate 48 and is held by an end stop plate 62 secured by bolts 64 to the plate 48.

The shaft 60 has cam plates 66 and 68 fixedly mounted thereon for rotation therewith. The cam plates 66 and 68 are identical and each defines a ramping spiral cam surface with an abrupt step 70. The cam follower for surfaces 68 is a pin 72 mounted in transverse opening 26 of ram 20. As pin 72 rides along the spiral ramp at an increasing distance from the center of rotation of shaft 60, the ram 20 retracts into the barrel bore 14 and hollow cap 34. The large spring 30 is compressed by flange 28 against the end cap 42 until the pin 72 drops off abrupt step 70. The ram 20 then moves forward under the force of the uncompressing spring 30 until it projects past end cap 34 and ram end 22 impacts the structure of the NSSS at the predetermined point. An accelerometer may thus be accurately calibrated with the repeatable known energy of the impact.

The shaft 60 is rotated by means of a crank arm 74 and roller handle 76 therefor fixed to the shaft. A small spring 78 in small counterbore 18 mechanically assists in the rebound of ram 20 during post-impact motion. The flange 28 prevents pin 72 from damaging the cam plates 66 and 68 by limiting the projection of ram end 22. A slot 80 accommodates the shaft 60 during reciprocation of ram 20.

The tool is conveniently operated by placing end cap 34 against the NSSS structure at the desired point, grasping the handle 50 with one hand and the handle 76 with the other and rotating the shaft 60 for one revolution thereby creating the desired standard impact.

I claim:

1. A tool for creating a standard repeatable impact on a structure to determine the response of an accelerometer to the impact of a known energy at a predetermined location on the structure, said tool comprising in combination:

a hollow barrel having an outer end and an inner end;
a ram having a first end and a second end reciprocally mounted within said barrel with said first end for alternate projection from and retraction into the outer end of said barrel;
a spring for biasing said ram in a direction toward the outer end of each barrel;
a housing mounted on the inner end of said barrel;
means for rotationally mounting a shaft in said housing;
means providing a cam surface for rotation with said shaft;
means for following said cam surface attached to said ram at said second end, said second end projecting from said inner end of said barrel into said housing;
means to rotate said shaft and said means providing a cam surface, thereby creating reciprocation of said ram through said means for following said cam surface as it alternately compresses said spring to an energy loaded position of ram retraction into said barrel and an energy expending uncompressed position of ram projection from said barrel to create a repeatable impact at the predetermined location on the structure which has been established by contact with the structure by the outer end of the barrel during retraction.

2. The tool combination of claim 1 in which the tool includes a second spring of biasing force opposite to and of less magnitude than the spring force which biases said ram in a direction toward the outer end of said barrel.

3. The tool combination of claim 1 in which a handle is mounted on the housing.

4. The tool combination of claim 1 in which the housing has a top plate and two spaced side plates between which said rotating shaft spans.

5. The tool combination of claim 1 in which the rotating shaft is rotated by manual crank means.

6. The tool combination of claim 1 in which the means providing a cam surface are two spaced cam plates on opposite sides of said ram and said means for following is a pin mounted on said ram.

* * * * *

UNITED STATES PATENT AND TRADEMARK OFFICE
CERTIFICATE OF CORRECTION

PATENT NO. : 4,967,587
DATED : November 6, 1990
INVENTOR(S) : Edward G. Sirica

It is certified that error appears in the above—identified patent and that said Letters Patent is hereby corrected as shown below:

Column 4, claim 1, line 7, delete the word "each" and insert therefor --said--.

Signed and Sealed this

Sixteenth Day of November, 1993

Attest:

BRUCE LEHMAN

Attesting Officer    Commissioner of Patents and Trademarks